(12) United States Patent
Forbes

(10) Patent No.: US 8,796,238 B2
(45) Date of Patent: Aug. 5, 2014

(54) SHORT RNA MIMETICS

(75) Inventor: Kevin Forbes, St. Louis, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 0 days.

(21) Appl. No.: 13/496,772

(22) PCT Filed: Sep. 13, 2010

(86) PCT No.: PCT/US2010/048597
§ 371 (c)(1),
(2), (4) Date: Apr. 5, 2012

(87) PCT Pub. No.: WO2011/034811
PCT Pub. Date: Mar. 24, 2011

(65) Prior Publication Data
US 2012/0184726 A1    Jul. 19, 2012

Related U.S. Application Data

(60) Provisional application No. 61/243,424, filed on Sep. 17, 2009.

(51) Int. Cl.
*C12N 15/11* (2006.01)

(52) U.S. Cl.
USPC .......................................... 514/44 A

(58) Field of Classification Search
USPC .......................................... 514/44 A
See application file for complete search history.

(56) References Cited

U.S. PATENT DOCUMENTS

| | | | |
|---|---|---|---|
| 2004/0180351 A1 | 9/2004 | Giese et al. | |
| 2005/0261218 A1 | 11/2005 | Esau et al. | |
| 2005/0266552 A1 * | 12/2005 | Doench et al. | 435/358 |
| 2006/0121466 A1 * | 6/2006 | Khvorova et al. | 435/6 |
| 2007/0185049 A1 | 8/2007 | Jadhav et al. | |
| 2009/0042298 A1 | 2/2009 | Houston, Jr. et al. | |
| 2009/0136957 A1 | 5/2009 | Ivanovska et al. | |
| 2012/0263738 A1 * | 10/2012 | Brown | 424/178.1 |
| 2012/0329857 A1 * | 12/2012 | Ge et al. | 514/44 A |

FOREIGN PATENT DOCUMENTS

| | | |
|---|---|---|
| WO | 2006/137941 A2 | 12/2006 |
| WO | 2009/029690 A1 | 3/2009 |
| WO | 2011/034811 A1 | 3/2011 |

OTHER PUBLICATIONS

International Search Report and Written Opinion from related application, PCT/US10/48597, dated Jan. 6, 2011, 8 pgs.

Czauderna et al., "Structural variations and stabilising modifications of synthetic siRNAs in mammalian cells", Nucleic Acids Research, 2003, pp. 2705-2716, vol. 31, No. 11.

McManus et al., "Gene silencing using micro-RNA designed hairpins", RNA, 2002, pp. 842-850, vol. 8.

Sipa et al., "Effect of base modifications on structure, thermodynamic stability, and gene silencing activity of short interfering RNA", RNA, 2007, pp. 1301-1316, vol. 13, No. 8.

Tomari et al., "A Protein Sensor for siRNA Asymmetry", Science, 2004, pp. 1377-1380, vol. 306.

* cited by examiner

*Primary Examiner* — Brian Whiteman
(74) *Attorney, Agent, or Firm* — Polsinelli PC

(57) ABSTRACT

The present invention provides synthetic oligonucleotides that mimic the function of short RNAs such as, for example, microRNAs or short interfering RNAs. In particular, the synthetic oligonucleotides comprise a duplex region comprising an unpaired bulge in one of the strands.

4 Claims, 5 Drawing Sheets

SHORT RNA MIMETICS

FIELD OF THE INVENTION

The present invention relates to synthetic oligonucleotides that mimic the function of short RNAs such as, for example, microRNAs or short interfering RNAs.

BACKGROUND OF THE INVENTION

MicroRNAs (miRNAs) and short interfering RNAs (siRNAs) regulate gene expression through a process termed RNA interference (RNAi). Mature miRNAs and siRNAs comprise a guide strand that is partially complementary to a target nucleic acid and an anti-guide or passenger strand that is complementary to the guide strand. Upon incorporation of the guide strand into the RNA-induced silencing complex (RISC), the guide strand base pairs with the target nucleic acid, which is then silenced by degradation and/or inhibition of translation. Several synthetic oligonucleotides are available that are able to silence specific target sequences, but they generally tend to also silence unintended targets. This non-specific silencing is termed off-targeting or off-target effects. Off-targeting may be mediated by erroneous entry of the passenger strand into RISC. There is a need, therefore, for improved synthetic oligonucleotides that mimic the effects of short RNAs with high specificity and minimal off-target effects.

SUMMARY OF THE INVENTION

Among the various aspects of the present invention is the provision of synthetic oligonucleotides that mimic the function of short RNAs. An oligonucleotide of the invention comprises a duplex region comprising a first strand whose sequence has at least about 90% sequence identity with a specific short RNA and a second strand whose sequence has at least about 60% complementarity to the first strand. Additionally, the duplex region comprises a bulge of one to four unpaired nucleotides in the second strand, wherein the bulge is located between any adjacent two of the six nucleotides located near the 3' end of the duplexed region of the second strand.

Another aspect of the present invention encompasses a kit for mimicking the function of a specific short RNA. The kit comprises at least one oligonucleotide, wherein the oligonucleotide comprises a first strand whose sequence has at least about 90% sequence identity with the specific short RNA and a second strand whose sequence has at least about 60% complementarity to the first strand. Additionally, the second strand comprises an insertion of one to four nucleotides near its 3' end such that upon base pairing between the first strand and the second strand to form a duplex region there is a bulge of unpaired nucleotides in the second strand, wherein the bulge is located between any adjacent two of the six nucleotides located near the 3' end of the duplexed region of the second strand.

A further aspect of the present invention provides a method for specifying an oligonucleotide that mimics the function of a specific short RNA. The method comprises specifying a first strand whose sequence has at least about 90% sequence identity with the specific short RNA; and specifying a second strand whose sequence has at least about 60% complementarity to the first strand, wherein the second strand comprises an insertion of one to four nucleotides near its 3' end such that when the first strand base pairs with the second strand to form a duplex region there is a bulge of unpaired nucleotides in the second strand. Moreover, the bulge is located between any adjacent two of the six nucleotides located near the 3' end of the duplexed region of the second strand Other aspects and features of the invention are described in more detail below.

DETAILED DESCRIPTION

Figure 1:
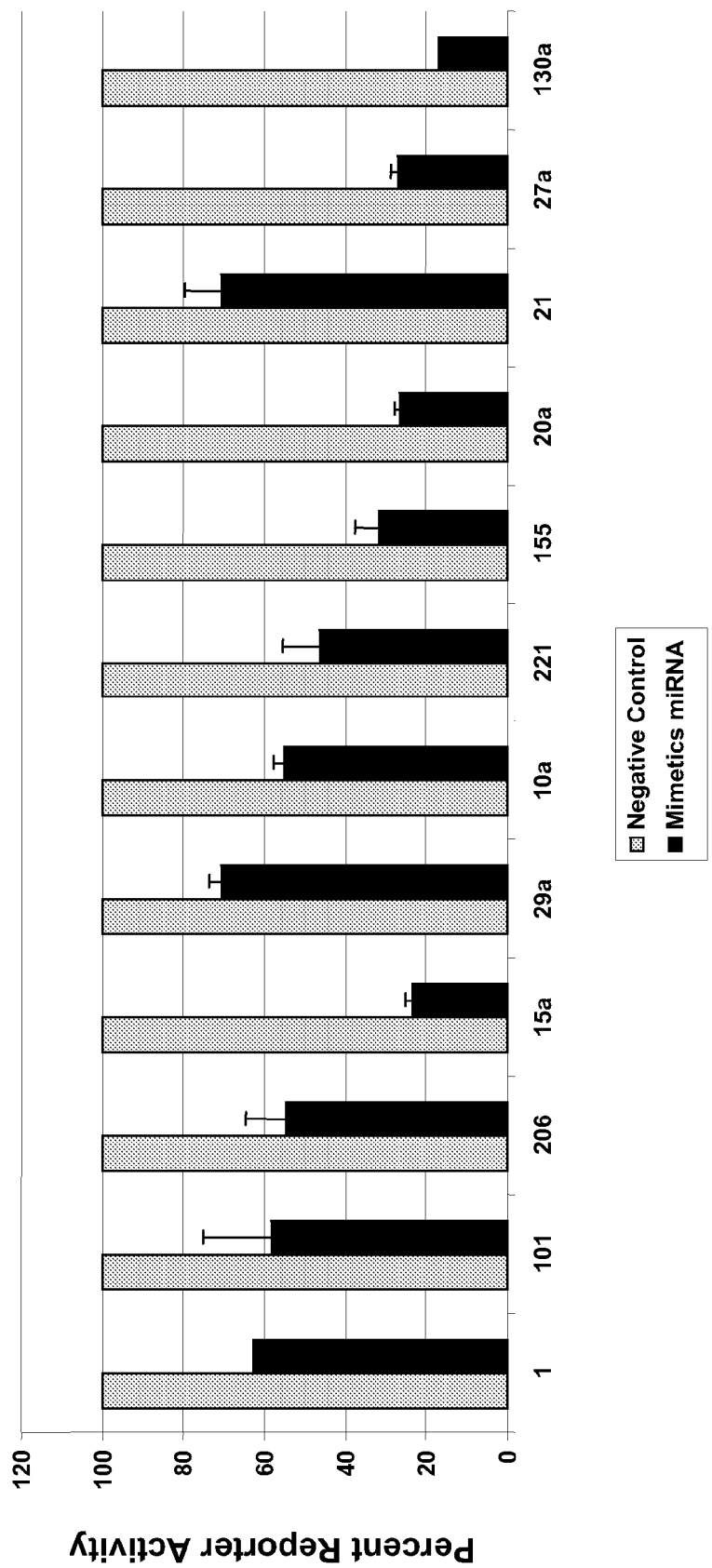
FIG. 1 demonstrates reporter knockdown by miRNA mimetics. Plotted is the relative percent of luciferase reporter activity in cells co-transfected with a particular target reporter nucleic acid sequence and a miRNA mimetic as indicated.

The present invention provides synthetic oligonucleotides that mimic the function of specific short RNAs with high specificity and with minimal off-target effects. Stated another way, the synthetic oligonucleotides of the invention are short RNA mimetics. In general, a synthetic oligonucleotide of the invention comprises a guide strand and a complementary passenger strand having an unpaired insertion, such that when the two strands base pair to form a duplex there is an unpaired bulge in the passenger strand. The bulge in the passenger strand helps ensure that the guide strand is incorporated into RISC because the bulge weakens base pairing at that end of the duplex, facilitating loading into the complex from the nearest 5'-end. The invention also provides methods for specifying oligonucleotides that mimic the function of specific short RNAs with high specificity, as well as kits comprising the oligonucleotides of the invention.

(I) RNA Mimetic Oligonucleotides

One aspect of the present invention comprises synthetic oligonucleotides that mimic the function of short RNAs. Non-limiting examples of suitable short RNAs include microRNAs (miRNAs), short interfering RNAs (siRNAs), small activating RNAs (saRNAs), short sense transcripts, short antisense transcripts, short non-coding transcripts, repeat associated siRNAs (rasiRNAs), transacting siRNAs (tsiRNAs), Piwi interacting RNAs (piRNAs), and 21-U RNAs. As used herein, the term "short RNA" refers to mature or fully processed short RNAs. The short RNA may be exogenous to the cell in which it functions. Alternatively, the short RNA may be endogenous to the cell in which it functions, i.e., it is transcribed from the genome. Endogenous short RNAs may be found in microbes, fungi, plants, invertebrates (e.g., nematodes, fruit flies, and the like), and vertebrates (e.g., frogs, zebrafish, rodents, and mammals such as companion animals, zoo animals, and humans).

In general, short RNAs function through RNA interference (RNAi) pathways and may regulate gene expression at several different levels. Those of skill in the art will appreciate that while short RNAs may be double stranded, they typically function as single-stranded entities (i.e., base pair with a target nucleic acid).

Short RNAs are generally less than about 100 nucleotides in length, and more preferably about 50 or fewer nucleotides in length. In various embodiments, the short RNA may be about 50, 45, 40, 35, 34, 33, 32, 31, 30, 29, 28, 27, 26, 25, 24, 23, 22, 21, 20, 19, 18, 17, 16, 15, 14, 13, or 12 nucleotides in length. In one preferred embodiment, the short RNA may range from 15 nucleotides to 35 nucleotides in length. In another preferred embodiment, the short RNA may range from 20 nucleotides to 24 nucleotides in length. In an exemplary embodiment, the short RNA may range from 21 nucleotides to 23 nucleotides in length.

(a) Oligonucleotide Structure

In general, the synthetic oligonucleotides of the invention comprise a duplex region in which one of the strands comprises an unpaired bulge. The duplex region of the oligonucleotide comprises a first strand whose sequence has at least about 90% sequence identity with a specific short RNA. The specific short RNA may be a miRNA, a siRNA, a saRNAs, a short sense transcript, a short antisense transcript, a short non-coding transcript, a rasiRNA, a tsiRNA, a piRNA, or a 21-U RNA. In preferred embodiments, the specific short RNA may be a miRNA or a siRNA. In some embodiments, the sequence of the first strand may be about 90%, 91%, 92%, 93%, 94%, 95%, 95%, 97%, 98%, or 99% identical to the specific short RNA. In another embodiment, the sequence of the first strand may be essentially identical to the specific short RNA.

The duplex region of the oligonucleotide also comprises a second strand whose sequence has at least about 60% complementarity to the first strand. In various embodiments, the sequence of the second strand may have about 60%, 62%, 64%, 66%, 68%, 70%, 72%, 74%, 76%, 78%, 80%, 82%, 84%, 86%, 88%, 90%, 92%, 94%, or 96% complementarity to the first strand.

The length of the duplex region of the oligonucleotide can and will vary. In general, length of the duplex region ranges from about 10 base pairs to about 50 base pairs in length. In various embodiments, the length of the duplex region of the oligonucleotide may range from about 12 base pairs to about 40 base pairs, from about 15 base pairs to about 35 base pairs, from about 18 base pairs to about 30 base pairs, or from about 20 base pairs to about 24 base pairs. In exemplary embodiments, the duplex region of the oligonucleotide may be 20 base pairs, 21 base pairs, or 22 base pairs in length.

The second strand also comprises an insertion of one to four nucleotides near its 3' end such that upon base pairing between the first strand and the second strand to form the duplex region, there is a bulge of unpaired nucleotides in the second strand. In general, the stability of the duplex is reduced as the length of the insertion (or bulge) is increased. In some embodiments, the insertion (or bulge) in the second strand may comprise three or four nucleotides. In preferred embodiments, the insertion (or bulge) in the second strand may comprise one or two nucleotides. In an exemplary embodiment, the insertion (or bulge) in the second strand may comprise one nucleotide.

The bulge of unpaired nucleotides in the second strand of the duplex region may be located between any adjacent two of the six nucleotides located near the 3' end of the duplexed region of the second strand. Stated another way, the bulge in the second strand may be located between the first and second nucleotides from the 3' end of the duplexed region of the second strand, between the second and third nucleotides from the 3' end of the duplexed region of the second strand, between the third and fourth nucleotides from the 3' end of the duplexed region of the second strand, between the fourth and fifth nucleotides closest to the 3' end of the duplexed region of the second strand, or between the fifth and sixth nucleotides from the 3' end of the duplexed region of the second strand. In an exemplary embodiment, the bulge in the second strand may be located between the third and fourth nucleotides from the 3' end of the duplexed region of the second strand. Without being bound by any particular theory, it is believed that the bulge in that region of the oligonucleotide increases the likelihood that the first strand, which is substantially identical to the specific short RNA, and not the second strand will be integrated into RISC. Thus, off-target effects are reduced or eliminated.

The second strand may further comprise a capping group at its 5' terminus. Non-limiting examples of suitable capping groups include amino groups, methyl groups, acetyl groups, carboxyl groups, carboxymethyl groups, and thiol groups. In an exemplary embodiment, the capping group at the 5' terminus of the second strand may be an amino group.

In some embodiments, the oligonucleotide may further comprise at least one 3' overhang, i.e., a single-stranded portion that extends beyond the duplex region. In various embodiments, the first strand, the second strand, or both may have a 3' overhang. The 3' overhang may range from about one nucleotide to about six nucleotides, or more preferably, from about one nucleotide to about three nucleotides in length. In an exemplary embodiment, the 3' overhang may comprise two nucleotides.

(b) Oligonucleotide Composition

In general, the nucleotides of the first strand that form the duplex region will be ribonucleotides. However, if the first strand comprises an optional 3' overhang, then the 3' overhang may be ribonucleotides or deoxyribonucleotides. Thus, the entire first stand may comprise ribonucleotides or a combination of ribonucleotides and deoxyribonucleotides. In contrast, the nucleotides of the second strand that form the duplex region may be ribonucleotides, deoxyribonucleotides, or combinations thereof. In one embodiment, the nucleotides of the second strand may be ribonucleotides. In another embodiment, the nucleotides of the second strand may be a combination of ribonucleotides and deoxyribonucleotides. In an exemplary embodiment, the nucleotides of the second strand that will form the duplex region and the bulge of the oligonucleotide may be ribonucleotides, while the optional 3' overhang may be deoxyribonucleotides. In general, the nucleotides of the bulge may comprise any nitrogenous base. In exemplary embodiments, the nucleotides of the bulge may comprise pyrimidine bases such as uracil, cytosine, or thymine. In exemplary embodiments, the bulge may comprise uridine, which is the smallest nucleotide according to the space-filling model.

The nucleotides of the oligonucleotide may comprise unmodified, modified, or derivatized nitrogenous base moieties and/or unmodified, modified, or derivatized sugar moieties. Additionally, the nucleotides of the oligonucleotide may be nucleotide analogs.

The heterocyclic base moiety of the nucleotide may be an unmodified purine base (e.g., adenine, guanine, hypoxanthine, or xanthine) or an unmodified pyrimidine base (e.g., cytosine, thymine, or uracil). Alternatively, the purine or pyrimidine base moiety may be a derivatized or modified by the replacement or addition of one of more atoms or groups. Examples of suitable modifications include, but are not limited to, alkylation, halogenation, thiolation, amination, amidation, acetylation, and combinations thereof. More specific modified bases include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. In preferred embodiments, the base moiety may be a standard purine or pyrimidine (i.e., adenine, cytosine, guanine, thymine, and uracil) base.

The sugar moiety of the nucleotide may be an acyclic sugar or a carbocyclic sugar. Suitable examples of an acyclic sugar include, but are not limited to glycerol (which may form a glycerol nucleic acid or GNA), threose (which may form a threose nucleic acid or TNA), erthrulose, erythrose, and so forth. Non-limiting examples of suitable carbocyclic sugars include pentoses (such as, arabinose, deoxyribose, lyxose, ribose, xylose, xylulose, etc., and derivatives thereof) and hexoses (such as, galactose, glucose, mannose, etc., and derivatives thereof). The sugar moiety may be isomeric, i.e., it may be the D-form or the L-form. The configuration of the sugar moiety may be alpha ($\alpha$) or beta ($\beta$). In preferred embodiments, the sugar moiety may be a $\beta$-D-ribose.

The sugar moiety of a nucleotide also may comprise a locked nucleic acid (LNA), in which the 2' and 4' carbons, or the 3' and 4' carbons, of the sugar moiety are connected with an extra bridge. The nucleotide may also comprise a sugar analog or substitute, such as a morpholine ring, which may be connected by a phosphorodiamidate linkage to form a morpholino, or a N-(2-aminoethyl)-glycine unit, which may be connected by a peptide bond to form a peptide nucleic acid (PNA). The sugar moiety of the nucleotide also may have a substituent at the 2' position or the 3' position of the molecule. The substituent may be selected from the group consisting of hydrogen, halogen, —R, —NHR, —NRR$^1$, —SR, and —OR, wherein R and R$^1$ are independently selected from the group consisting of hydrogen, hydrocarbyl, and substituted hydrocarbyl. Preferably, R may be alkyl (such as, e.g., methyl, ethyl, propyl, isopropyl, etc), acyl, alkenyl, or aryl.

The nucleotides of the oligonucleotide may be connected by phosphorus-containing linkages, non-phosphorus-containing linkages, or combinations thereof. Examples of suitable phosphorus-containing linkages include, but are not limited to, phosphodiester, phosphorothioate, phosphorodithioate, phosphoramidate, alkylphosphoramidate, aminoalkylphosphoramidate, thionophosphoramidate, alkylphosphonothioate, arylphosphonothioate, thiophosphate, alkyl phosphonate, methylphosphonate, alkylenephosphonate, hydrogen phosphonate, phosphotriester, ethylphosphotriester, thionoalkylphosphotriester, phosphinate, borano phosphate ester, selenophosphate, phosphoroselenoate, phosphorodiselenoate, phosphoropiperazidate, phosphoroanilothioate, and phosphoroanilidate linkages. Non-limiting examples of suitable non-phosphorus-containing linkages include alkyl, amide, amine, aminoethyl glycine, borontrifluoridate, carbamate, carbonate, cycloalkyl, ether, formacetal, glycol, hydroxylamine, hydrazino, ketone, methylenehydrazo, methylenedimethylhydrazo, methyleneimino, methylene(methylimino), methylester, oxime, sulfonamide, sulfone, thioamidate, siloxane, silyl, thioformacetal, and urea linkages. In preferred embodiments, the internucleotide linkages may be phosphodiester or phosphorothioate linkages. In an exemplary embodiment, the internucleotide linkages may be phosphodiester linkages.

The oligonucleotides of the invention may be synthesized according to standard techniques using phosphoramidite monomers (e.g., Methods in Molecular Biology, Vol 20, Protocols for Oligonucleotides and Analogs, Agrawal, ed., Humana Press, Totowa, N.J., 1993).

(c) Preferred Embodiments

In preferred embodiments, the first strand ranges from about 20 to 24 ribonucleotides in length; the second strand ranges from about 21 to 25 ribonucleotides in length and has a 3' overhang of two deoxyribonucleotides; the duplex region of the oligonucleotide ranges from about 20 to 24 base pairs in length with a one nucleotide bulge located between the third and fourth nucleotides from the 3' end of the duplexed region of the second strand. In an iteration of this embodiment, the unpaired nucleotide in the bulge is a uridine residue. In other iterations of this embodiment, the first strand further comprises a 3' overhang of two nucleotides. In exemplary embodiments, the specific short RNA is a human miRNA.

(II) Methods for Specifying RNA Mimetic Oligonucleotides

Another aspect of the invention provides methods for specifying an oligonucleotide that mimics the function of a specific short RNA. The method comprises specifying a first strand whose sequence has at least about 90% sequence identity with the specific short RNA; and specifying a second strand whose sequence has at least about 60% complementarity to the first strand. Additionally, the second strand comprises an insertion of one to four nucleotides near its 3' end such that when the first strand base pairs with the second strand to form a duplex region there is a bulge of unpaired nucleotides in the second strand, wherein the bulge is located between any adjacent two of the six nucleotides located near the 3' end of the duplexed region of the second strand. Together the two strands form an oligonucleotide that mimics the function of a specific short RNA with minimal off-targeting. Aspects of the oligonucleotides of the invention are detailed above in section (I).

(III) Kits

A further aspect of the present invention encompasses kits for mimicking the function of a specific short RNA. A kit comprises at least one oligonucleotide that mimics the function of a specific short RNA. The oligonucleotides of the invention are detailed above in section (I). In some embodiments, the two strands of the oligonucleotide may be provided together in the kit as a duplex. In other embodiments, the two strands of the oligonucleotide may be provided separately in the kit. The kit may also comprise nuclease-free water or nuclease-free buffers for diluting the oligonucleotides of the kit.

(IV) Uses of the Oligonucleotides of the Invention

Yet another aspect of the present invention provides methods for using the oligonucleotides of the invention. In general, the oligonucleotides of the invention may be used to study the biological role of specific short RNAs through gain of function, or to screen for short RNAs that regulate gene function or affect specific cellular pathways or processes (such as, e.g., cell proliferation, differentiation, development, apoptosis, etc.). Additionally, the oligonucleotides of the invention also may be used to identify the target nucleic acids of specific short RNAs, or to evaluate the mechanism and potency of miRNA inhibitors or other short RNA inhibitors.

To examine the function of specific short RNAs, the oligonucleotides of the invention may be introduced into a cell by any of several well-known techniques such as, for example, electroporation, liposomal or other vesicular delivery systems, direct cell fusion, viral carriers, osmotic shock, application of protein carriers or antibody carriers, and calcium-phosphate mediated transfection.

To facilitate entry into the cell, an oligonucleotide may be chemically modified to enhance its permeability. Examples of receptor mediated endocytotic systems whereupon chemical conjugation to the oligonucleotide may be used to enhance cellular uptake by targeting a specific cell surface receptor include, but are not limited to, galactose, mannose, mannose-6-phosphate, transferrin, asialoglycoproteins, water soluble vitamins (e.g. transcobolamin, biotin, ascorbic acid, folates, etc.) any pharmacological agent or analog that mimics the binding of a water soluble vitamin, alpha-2 macroglobulins, insulin, epidermal growth factor, or attachment to an antibody against a surface protein of the target cell as in the case of the so-called immunotoxins. Chemical conjugation of the oligonucleotide may also include apolar substituents such as hydrocarbon chains or aromatic groups and/or polar substituents such as polyamines to further enhance intracellular uptake. Chemical conjugation of the oligonucleotide to an exogenous molecule may be achieved by covalent, ionic or hydrogen bonding either directly or indirectly by a linking group. Preferably, the exogenous molecule may be covalently linked to the oligonucleotide using techniques are well known in the art.

Various methods of formulation and administration of the oligonucleotide are known to those skilled in the medical arts (Avis, K. in Remington's Pharmaceutical Sciences, 1985, pp. 1518-1541, Gennaro, A. R., ed., Mack Publishing Company, Easton, Pa.). Such methods of administration may include, but are not limited to, surface application, oral, or parenteral routes, injection into joints, subcutaneous injection, or other pharmaceutical methods of delivery. Surface application of the oligonucleotide includes topical application to such surfaces as skin, eyes, lungs, nasal or oral passages, ears, rectum, vagina, and the like. Appropriate means for parenteral administration include 5% dextrose, normal saline, Ringer's solution and Ringer's lactate. The oligonucleotide may be stored as a lyophilized powder and reconstituted when needed by addition of an appropriate salt solution.

DEFINITIONS

To facilitate understanding of the invention, several terms are defined below.

The term "acyl," as used herein alone or as part of another group, denotes the moiety formed by removal of the hydroxy group from the group COON of an organic carboxylic acid, e.g., RC(O), wherein R is $R^1$, $R^1O-$, $R^1R^2N-$, or $R^1S-$, $R^1$ is hydrocarbyl, heterosubstituted hydrocarbyl, or heterocyclo, and $R^2$ is hydrogen, hydrocarbyl or substituted hydrocarbyl.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups having at least one carbon-carbon double bond that preferably contain from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

As used herein, the terms "complementary" or "complementarity" refer to the association of double-stranded nucleic acids by base pairing through specific hydrogen bonds. The base paring may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some of the base pairs are complementary. The bases that are not complementary are "mismatched." Complementarity may also be complete (i.e., 100%), if all the base pairs of the duplex region are complementary.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "off-target," as used herein, refers to any effect other than silencing of the intended target nucleic acid.

As used herein, the term "sequence identity" refers to the extent in which two nucleotide sequences are invariant, i.e., the two sequences have the same nucleotide at the same position. Sequence identity is generally expressed as a percentage. Two nucleotide sequences that are identical in sequence and length have 100% sequence identity.

The term "short RNA" as used herein refers to RNA molecules that function through RNA interference. Short RNAs are generally less than about 100 nucleotides in length. Non-limiting examples of short RNAs include microRNAs (miRNAs), short interfering RNAs (siRNAs), small activating RNAs (saRNAs), short sense transcripts, short antisense transcripts, short non-coding transcripts, repeat associated siRNAs (rasiRNAs), transacting siRNAs (tsiRNAs), Piwi interacting RNAs (piRNAs), and 21-U RNAs The "substituted hydrocarbyl," "substituted alkyl," "substituted alkenyl," "substituted aryl," and "substituted heteroaryl" moieties described herein are hydrocarbyl, alkyl, alkenyl, aryl, and heteroaryl moieties, respectively, that are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters, and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds and processes without departing from the scope of the invention, it is intended that all matter contained in the above description and in the examples given below, shall be interpreted as illustrative and not in a limiting sense.

EXAMPLES

The following examples detail various embodiment of the invention.

Example 1

Reporter Knockdown by miRNA Mimetics

The silencing effects of miRNA mimetics, as detailed above, were examined using a gene fusion reporter assay (psiCHECK™, Promega Corp., Madison, Wis.). For this, target sequences were subcloned into psiCHECK-2 vectors such that the target sequence was immediately downstream of the translation stop codon of the *Renilla* luciferase gene, hRluc. Table 1 lists the target sequences and the corresponding microRNA mimetic (the insertion in the anti-guide or passenger strand is shaded gray). Cells were co-transfected with the fusion vector and the appropriate miRNA mimetic, and relative luciferase activity was monitored as detailed in the manufacture's instruction manual.

FIG. 1 presents the relative reporter activity in the absence and presence of the miRNA mimetic. The mimetics decreased reporter activity from about 25% to more than 80%. These data suggests that all the guide strands from the miRNA mimetics were loaded into RISC and targeted the target sequence within the reporter. Since decreased reporter activity was observed with all the miRNA mimetics (FIG. 1), these finding suggests that the microRNA mimetic design presented here can be applied to all known small RNA designs.

TABLE 1

Target Sequences and miRNA Mimetics

| Target Gene | miRNA Mimetic | Sequence of miRNA mimetic | SEQ ID NO: |
|---|---|---|---|
| G6PD | miR-1 | NH$_2$-AUACAUACUUCUUUACAUGUCCATT<br>\|\|\|\|\|\|\|\|\|\|\|\|\|\|\|\|\|\|\| \|\|\|<br>UAUGUAUGAAGAAAUGUA-AGGU-5' | 1<br><br>2 |
| MYCN | miR-101 | NH$_2$-UUCAGUUAUCACAGUACUGGUATT<br>\|\|\|\|\|\|\|\|\|\|\|\|\|\|\|\|\|\|\| \|\|\|<br>AAGUCAAUAGUGUCAUGA-CAU-5' | 3<br><br>4 |
| GJA1 | miR-206 | NH$_2$-CCACACACUUCCUUUACAUUGCCATT<br>\|\|\|\|\|\|\|\|\|\|\|\|\|\|\|\|\|\|\| \|\|\|<br>GGUGUGUGAAGGAAUGUAA-GGU-5' | 5<br><br>6 |
| BCL2 | miR-15a | NH$_2$-AUACAUACUUCUUUACAUUGCCATT<br>\|\|\|\|\|\|\|\|\|\|\|\|\|\|\|\|\|\|\| \|\|\|<br>UAUGUAUGAAGAAAUGUAA-GGU-5' | 7<br><br>8 |
| DNMT | miR-29a | NH$_2$-UAACCGAUUUCAGAUGGUGUCUAUT<br>\|\|\|\|\|\|\|\|\|\|\|\|\|\|\|\|\|\|\| \|\|\|<br>AUUGGCUAAAGUCUACCAC-GAU-5' | 9<br><br>10 |
| HOXD10 | miR-10a | NH$_2$-CACAAAUUCGGAUCUACAGGUGUATT<br>\|\|\|\|\|\|\|\|\|\|\|\|\|\|\|\|\|\|\| \|\|\|<br>GUGUUUAAGCCUAGAUGUCC-CAU-5' | 11<br><br>12 |
| p27KIP1 (3'UTR) | miR-221 | NH$_2$-GAAACCCAGCAGACAAUGUAGGCUTT<br>\|\|\|\|\|\|\|\|\|\|\|\|\|\|\|\|\|\|\| \|\|\|<br>CUUUGGGUCGUCUGUUACAU-CGA-5' | 13<br><br>14 |
| AT1R | miR-155 | NH$_2$-ACCCCUAUCACGAUUAGCAUGUAATT<br>\|\|\|\|\|\|\|\|\|\|\|\|\|\|\|\|\|\|\| \|\|\|<br>UGGGGAUAGUGCUAAUCGUA-AUU-5' | 15<br><br>16 |
| 20a si | miR-20a | NH$_2$-CUACCUGCACUAUAAGCACUGUUATT<br>\|\|\|\|\|\|\|\|\|\|\|\|\|\|\|\|\|\|\| \|\|\|<br>GAUGGACGUGAUAUUCGUGA-AAU-5' | 17<br><br>18 |
| 21 si | miR-21 | NH$_2$-UCAACAUCAGUCUGAUAAGGCUATT<br>\|\|\|\|\|\|\|\|\|\|\|\|\|\|\|\|\|\|\| \|\|\|<br>AGUUGUAGUCAGACUAUUC-GAU-5' | 19<br><br>20 |
| 27a si | miR-27a | NH$_2$-GCGGAACUUAGCCACUGUGGAATT<br>\|\|\|\|\|\|\|\|\|\|\|\|\|\|\|\|\|\|\| \|\|\|<br>CGCCUUGAAUCGGUGACA-CUU-5' | 21<br><br>22 |
| 130a si | miR-130a | NH$_2$-AUGCCCUUUUAACAUUGCAGCUGTT<br>\|\|\|\|\|\|\|\|\|\|\|\|\|\|\|\|\|\|\| \|\|\|<br>UACGGGAAAAUUGUAACGU-GAC-5' | 23<br><br>24 |

Example 2

Passenger Strand Off-Target Effects

To examine possible off-target effects of the passenger strand, several miRNA-206 mimetics were prepared with different passenger strands. For example, the passenger strands had different complementary (e.g., 100% or about 95%) to the target sequence, had different lengths, and/or differed in the presence of the 5' amino group. The sequences of the target and passenger strands of the mimetics are shown in Table 2. The targeted region of the target sequence is underlined. The miRNA-206 mimetics were co-transfected with the fusion reporter vector (harboring the target sequence GJA1) essentially as described in Example 1.

Figure 2:
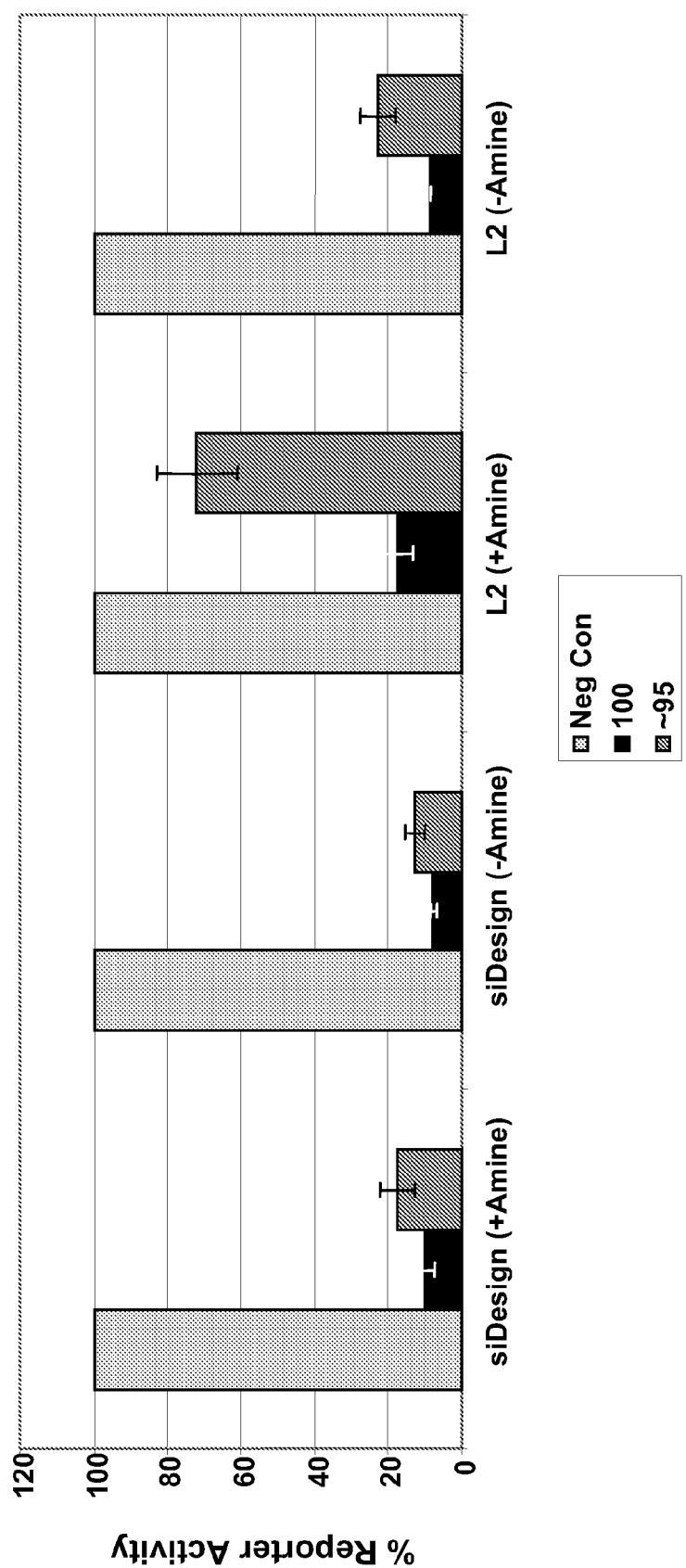
FIG. 2 shows passenger strand off-target effects. Plotted is the relative percent of luciferase reporter activity in cells co-transfected with a particular target reporter nucleic acid sequence and the miRNA-206 mimetic with different passenger strands as indicated. 100 and ~95 refer to the mean percent target sequence complementarity of the mimetic to the passenger strand.

The results are presented in FIG. 2. In general, the passenger strands had off-target effects. The exception was the L2(+amine) miRNA mimetic in which decreased reporter activity via the passenger strand of a miRNA mimetic was reduced when the target/mimetic complementarity was ~95%. This reduction was not observed with the siDesign mimetics. These findings suggest that having the extra base within the 3' end of the passenger strand either reduced loading into RISC or affected potential binding to a non-specific target within the human genome/transcriptome.

TABLE 2 miRNA-206 Passenger Strand siTargets

| Name and Sequence | | SEQ ID NO: |
|---|---|---|
| 206L2-N1 | 5'-UCGAAGAGCCAAAUUCUGUCUCCUUGG-AAUGUA-AGGAAGUGUGUGGACACCAAUGGCUUUCUAGAGCU | 25 |
| 206L2-DT | TTACCṶUUACAUUCCUUCACACACC-5' | 26 |
| 206L2-DT1 | TTACCṶUUACAUUCCUUCACACA-5' | 27 |
| si | TTACC-UUACAUUCCAACACACAA-5' | 28 |
| 206L2 | 5'-UCGAAGAGCCAAAUUCUGUCUCCUUGGAAAUGUA-AGGAAGUGUGUGGACACCAAUGGCUUUCUAGAGCU | 29 |
| 206L2-DT | TTACCṶUUACAUUCCUUCACACACC-5' | 26 |
| 206L2-DT1 | TTACCṶUUACAUUCCUUCACACA-5' | 27 |
| si | TTACC-UUACAUUCCAACACACACC-5' | 28 |

Similar experiments were performed for miRNA-101 mimetics. The sequences of the target (i.e., MYCN) and the passenger strands of various mimetics are shown in Table 3.

Figure 3:
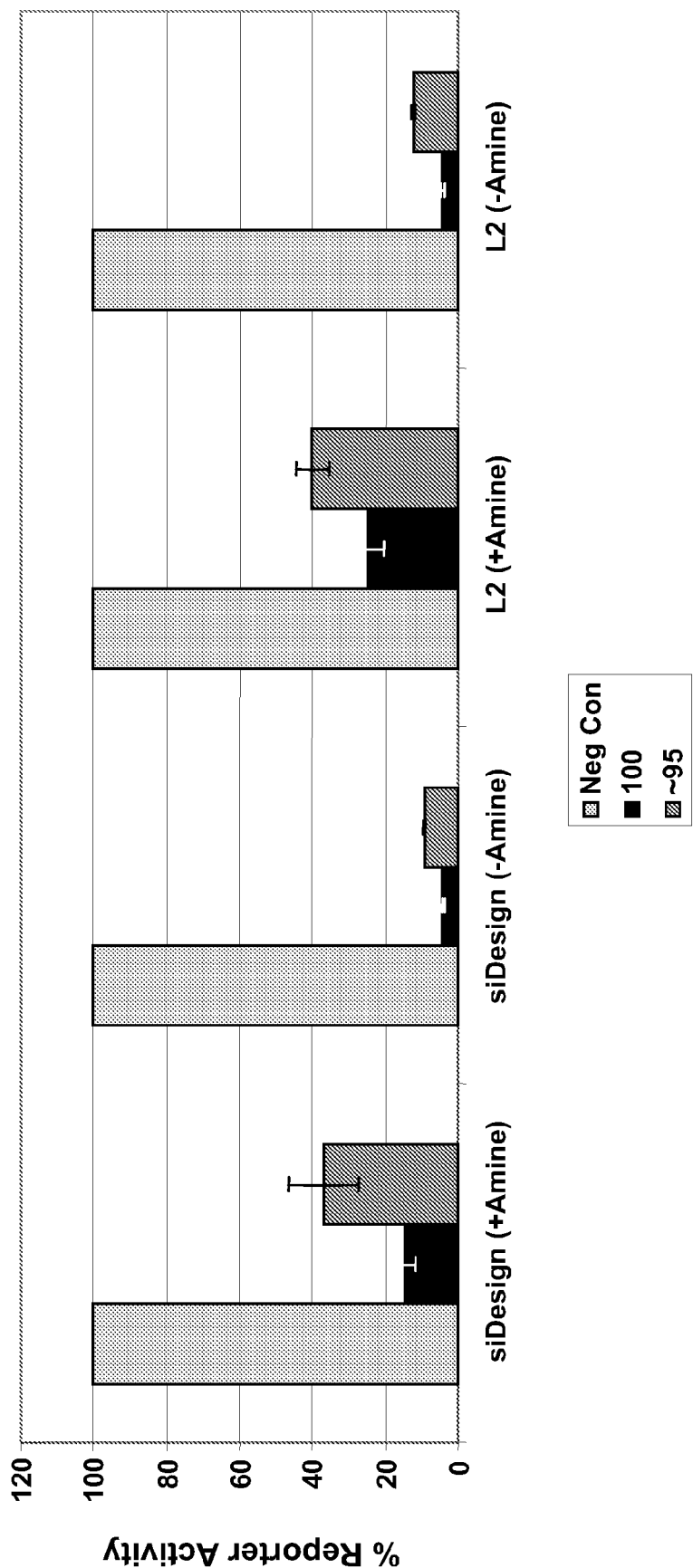
FIG. 3 illustrates passenger strand off-target effects. Plotted is the relative percent of luciferase reporter activity in cells co-transfected with a particular target reporter nucleic acid sequence and the miRNA-101 mimetic with different passenger strands as indicated. 100 and ~95 refer to the mean percent target sequence complementarity of the mimetic to the passenger strand.

As seen in FIG. 3, decreased reporter activity via the passenger strand of a miRNA mimetic was reduced with the L2(+amine) miRNA mimetic, when the target/mimetic complementarity was 100% and ~95%. The same reduction was observed for the siDesign(+amine) miRNA mimetic but not to the same extent at the 100% complementarity level with L2(+amine) miRNA mimetic. Once more, these data suggest that having the extra base within the 3' end of the passenger strand either reduced loading into RISC or affected potential binding to a non-specific target within the human genome/transcriptome.

TABLE 3 miRNA-101 Passenger Strand siTargets

| Name and Sequence | | SEQ ID NO: |
|---|---|---|
| 101L2-N1 | UCGAAGAAAUAUAUUGUUAAUAC-AGUACUGUGAUAACUGAACUAAUUCUUACACUGGCU | 30 |
| 101L2-DT | TTAUGṶUCAUGACACUAUUGACUU | 31 |
| 101L2-DT1 | TTAUGṶUCAUGACACUAUUGAC | 32 |
| si | AUG-UCAUGACACUAUUGACUU | 33 |
| 101L2 | UCGAGAAAUAUAUUGUUAA UACAAGUACUGUGAUAA-CUGAACUAAUUCUUACACUGGCU | 34 |
| 101L2-DT | TTAUGṶUCAUGACACUAUUGACUU | 31 |
| 101L2-DT1 | TTAUGṶUCAUGACACUAUUGAC | 32 |
| si | AUG-UCAUGACACUAUUGACUU | 33 |

Example 3

Guide Strand Loading

Figure 4:
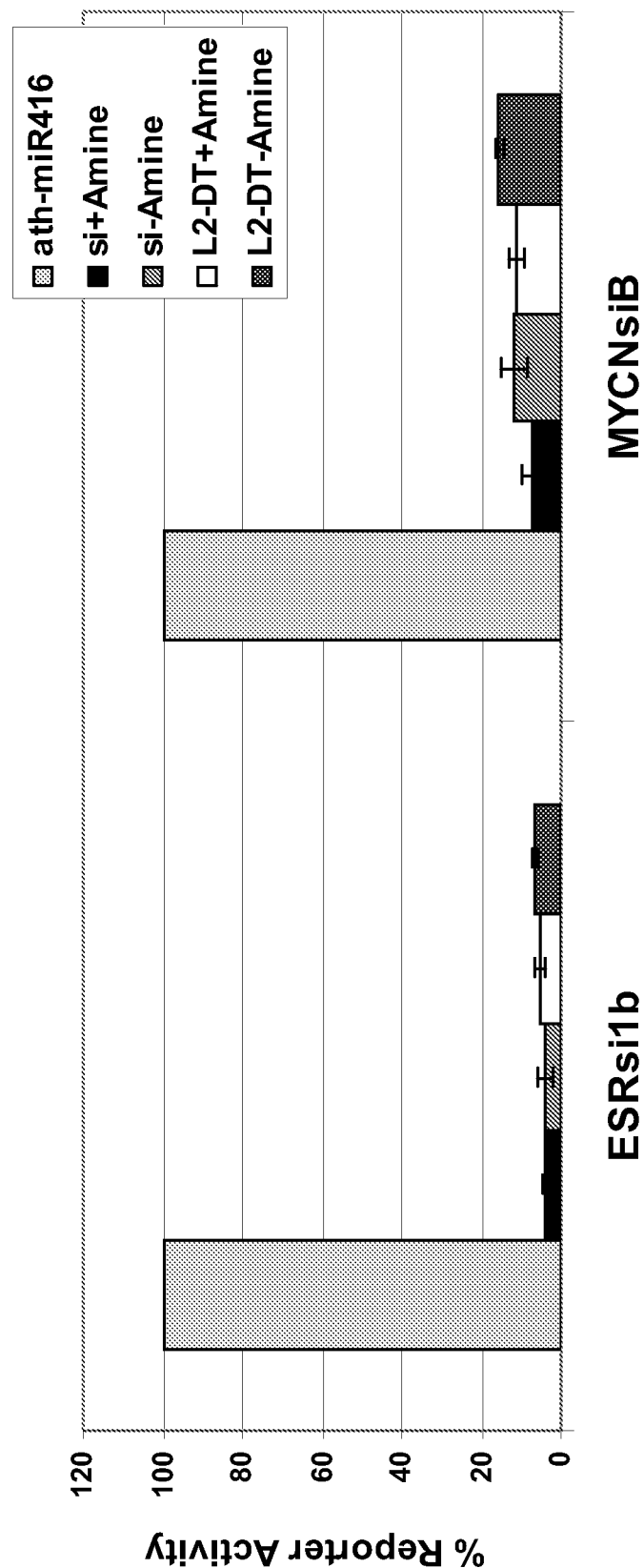
FIG. 4 demonstrates guide strand loading. Plotted is the relative percent of luciferase reporter activity in cells co-transfected with a particular target reporter nucleic acid sequence and the miRNA-206 or miRNA-101 mimetic as indicated.

To examine the specificity of guide strand loading, the mimetics of miRNA-206 or miRNA-101 were co-transfected with a fusion reporter vector carrying a target sequence that was 100% complementary to the corresponding guide strand. Reporter activity was monitored essentially as described in Example 1. Table 4 presents the sequences of the guide strands and the targets. As shown in FIG. 4, all of the guide strands loaded properly. Therefore, these data suggest that regardless of the passenger strand design used within the mimetic, the guide strand can be loaded into RISC and stimulate or knockdown its corresponding target(s). In this example, knockdown was observed.

TABLE 4

Guide Strand siTargets

| Name and Sequence | | SEQ ID NO: |
|---|---|---|
| ESRsiIB (miR206): | | |
| TCGAGAGCCAAATTCTGTCTCCT<u>CCACACACTTCCTTACATTCCA</u>ACACCAATGGCTTTCTAGAGC | | 35 |
| Mature miRNA | GGUGUGUGAAGGAAUGUAAGGU | 36 |
| MYCNsi2B (miR101): | | |
| TCGAGAAATATATTGTTAA<u>TCAGTTATCACAGTACTGTA</u>CTAATTCTTACACTGGC | | 37 |
| Mature miRNA | AAGUCAAUAGUGUCAUGACAU | 38 |

Example 4

Structure of miRNA Mimetics

Several miRNA mimetics with different structures were designed and tested for their ability to mimic the miRNA of interest. For example, miRNA mimetics were designed with one or two nucleotide inserts (or bulges), mismatched regions, and combinations thereof. Table 5 presents the sequences of miRNA mimetics prepared for miR206 (5'-UGGAAUGUAAGGAAGUGUGUGG-3'; SEQ ID NO:39) (the insertions and mismatched regions are shaded gray). Table 6 presents sequences of miRNA mimetics prepared for miR101-1 (5'-UACAGUACUGUGAUAACUGAA-3'; SEQ ID NO:58). The silencing effects of the miRNA mimetics were analyzed using the gene fusion reporter assay essentially as described in Example 1.

Figure 5:
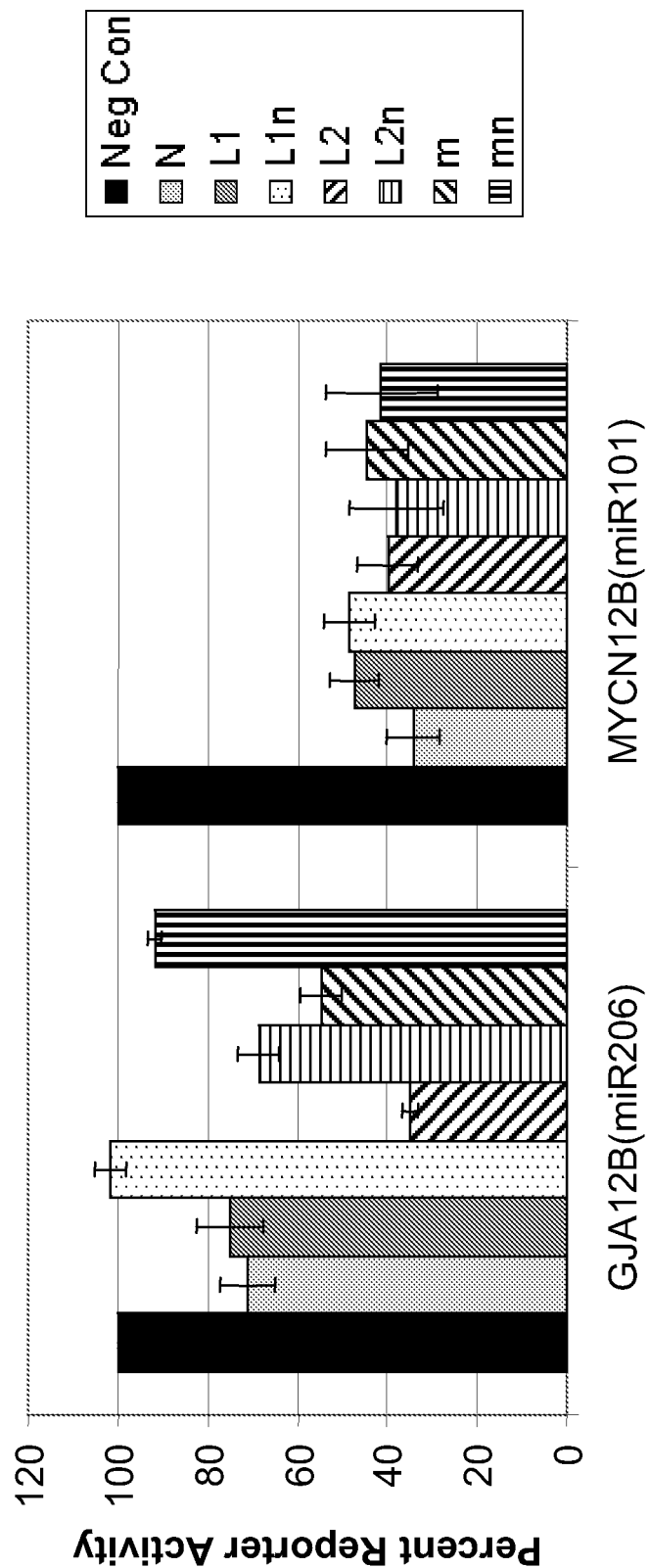
FIG. 5 illustrates the efficacy of miRNA mimetics having different designs or structures. Plotted is the relative percent of luciferase reporter activity in cells co-transfected with a particular target reporter nucleic acid sequence and miRNA-206 or miRNA-101 mimetic as indicated.

FIG. 5 presents the percentage of reporter activity in the presence of each miRNA mimic. Among the series of miR206 mimetics, miR206L2 comprising a single nucleotide bulge in the passenger strand, was the most effective miRNA mimetic. The data from the series of miR101 mimetics revealed that all reduced reporter activity to about the same degree. Therefore, these findings suggest that the L2 passenger strand design (Table 5) had no effect on guide strand loading and can be universally applied to microRNA mimetic designs (Table 1) and all known small RNAs.

TABLE 5 miR206 Mimetics

| Name | Sequence | SEQ ID NO: |
|---|---|---|
| miR206 | 5'-CCACAUGCUUCUUUAUAUCCCATT<br>\|\|\|\|\|\|\|\|\|\|\|\|\|\|\|\|\|\|\|\|\|\|\|<br>TTGGUGUGUGAAGGAAUGUA-AGGU-5' | 40<br><br>41 |
| miR206L1 | 5'-CCACACACUUCCUUACAUUAUCCATT<br>\|\|\|\|\|\|\|\|\|\|\|\|\|\|\|\|\|\|\|\|\|\|\|\|<br>TTGGUGUGUGAAGGAAUGUAA-GGU-5' | 42<br><br>43 |
| miR206L1-n | 5'-CCACACACUUCUUUAUAUUAUCCATT<br>\|\|\|\|\|\|\|\|\|\|\|\|\|\|\|\|\|\|\|\|\|\|\|\|<br>TTGGUGUGUGAAGGAAUGUAA-GGU-5' | 44<br><br>43 |
| miR206L2 | 5'-CCACACACUUCCUUACAUUUCCATT<br>\|\|\|\|\|\|\|\|\|\|\|\|\|\|\|\|\|\|\|\|\|\|\|\|<br>TTGGUGUGUGAAGGAAUGUAA-GGU-5' | 45<br><br>43 |

TABLE 5-continued miR206 Mimetics

| Name | Sequence | SEQ ID NO: |
|---|---|---|
| miR206L2-n | 5'-CCACACACUUCUUUAUAUUUCCATT<br>\|\|\|\|\|\|\|\|\|\|\|\|\|\|\|\|\|\|\|\|\|\|\|\|<br>TTGGUGUGUGAAGGAAUGUAA-GGU-5' | 46<br><br>43 |
| miR206mm | 5'-CCACACACUUCCUUACAGACCATT<br>\|\|\|\|\|\|\|\|\|\|\|\|\|\|\|\|\|\|\|\|\|\|<br>TTGGUGUGUGAAGGAAUGUAAGGU-5' | 47<br><br>43 |
| miR206mm-n | 5'-CCACACACUUCUUUAUACACCATT<br>\|\|\|\|\|\|\|\|\|\|\|\|\|\|\|\|\|\|\|\|\|\|<br>TTGGUGUGUGAAGGAAUGUAAGGU-5' | 48<br><br>43 |

TABLE 6 miR101-1 Mimetics

| Name | Sequence | SEQ ID NO: |
|---|---|---|
| miR101-1 | 5'-CUCAGUUAUCACAGUGCUGAUGTT<br>\|\|\|\|\|\|\|\|\|\|\|\|\|\|\|\|\|\|\|\|\|\|<br>TTAAGUCAAUAGUGUCAUGAC-AU-5' | 49<br><br>50 |
| miR101-2 | 5'-UUCGGUUAUCAUGGUACCGAUG<br>\|\|\|\|\|\|\|\|\|\|\|\|\|\|\|\|\|\|\|\|\|<br>TTAAGUCAAUAGUGUCAUGAC-AU-5' | 51<br><br>50 |
| miR101L1 | 5'-UUCAGUUAUCACAGUACUUUGUATT<br>\|\|\|\|\|\|\|\|\|\|\|\|\|\|\|\|\|\|\|\|\|\|<br>TTAAGUCAAUAGUGUCAUGA-CAU-5' | 52<br><br>50 |
| miR101L1-n | 5'-UUCAGUUAUCAUGGUACUUUGUATT<br>\|\|\|\|\|\|\|\|\|\|\|\|\|\|\|\|\|\|\|\|\|\|<br>TTAAGUCAAUAGUGUCAUGA-CAU-5' | 53<br><br>50 |
| miR101L2 | 5'-UUCAGUUAUCACAGUACUUGUATT<br>\|\|\|\|\|\|\|\|\|\|\|\|\|\|\|\|\|\|\|\|\|\|\|\|<br>TTAAGUCAAUAGUGUCAUGA-CAU-5' | 54<br><br>50 |
| miR101L2-n | 5'-UUCAGUUAUCAUGGUACUUGUATT<br>\|\|\|\|\|\|\|\|\|\|\|\|\|\|\|\|\|\|\|\|\|\|<br>TTAAGUCAAUAGUGUCAUGA-CAU-5' | 55<br><br>50 |
| miR101mm | 5'-UUCAGUUAUCACAGUAUCGUATT<br>\|\|\|\|\|\|\|\|\|\|\|\|\|\|\|\|\|\|\|\|<br>TTAAGUCAAUAGUGUCAUGACAU-5' | 56<br><br>50 |
| miR101mm-n | 5'-UUCAGUUAUCAUGGUAUCGUATT<br>\|\|\|\|\|\|\|\|\|\|\|\|\|\|\|\|\|\|\|<br>TTAAGUCAAUAGUGUCAUGACAU-5' | 57<br><br>50 |

What is claimed is:

1. A synthetic oligonucleotide comprising a duplex region comprising a first strand whose sequence has at least about 90% sequence identity with a specific short RNA and a second strand whose sequence has at least about 60% complementarity to the first strand, wherein the duplex region comprises a bulge of one to four unpaired nucleotides in the second strand, the bulge being located between the third nucleotide and the fourth nucleotide from the 3' end of the duplexed region of the second strand.

2. The synthetic oligonucleotide of claim 1, wherein the specific short RNA is a microRNA; the first strand comprises ribonucleotides; the second strand comprises ribonucleotides and has a 3' overhang of two deoxyribonucleotides; the second strand comprises a 5' amino group; the duplex region is from about 18 base pairs to about 30 base pairs in length; the bulge comprises one or two unpaired nucleotides; and the bulge is located between the third nucleotide and the fourth nucleotide from the 3' end of the duplexed region of the second strand.

3. A kit for mimicking the function of a specific short RNA, the kit comprising at least one oligonucleotide, wherein each oligonucleotide comprises a first strand whose sequence has at least about 90% sequence identity with the specific short RNA and a second strand whose sequence has at least about 60% complementarity to the first strand; the second strand comprising an insertion of one to four nucleotides near its 3' end such that upon base pairing between the first strand and the second strand to form a duplex region there is a bulge of unpaired nucleotides in the second strand, wherein the bulge is located between the third nucleotide and the fourth nucleotide from the 3' end of the duplexed region of the second strand.

4. A method for preparing an oligonucleotide that mimics the function of a specific short RNA, the method comprising:
 a) providing a first strand whose sequence has at least about 90% sequence identity with a specific short RNA;
 b) providing a second strand whose sequence has at least about 60% complementarity to the first strand, the second strand comprising an insertion of one to four nucleotides near its 3' end; and
 c) allowing the first strand to base pair with the second strand to form a duplex region, wherein the second strand has a bulge of unpaired nucleotides located between the third nucleotide and the fourth nucleotide from the 3' end of the duplexed region of the second strand.

* * * * *

SEQUENCE LISTING

```
<160> NUMBER OF SEQ ID NOS: 58

<210> SEQ ID NO 1
<211> LENGTH: 25
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
```

<223> OTHER INFORMATION: DNA only

<400> SEQUENCE: 1
auacauacuu cuuuacauuu ccatt                                              25

<210> SEQ ID NO 2
<211> LENGTH: 22
<212> TYPE: RNA
<213> ORGANISM: Homo sapiens

<400> SEQUENCE: 2
uggaauguaa agaaguaugu au                                                 22

<210> SEQ ID NO 3
<211> LENGTH: 24
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(22)
<223> OTHER INFORMATION: RNA only
<220> FEATURE:
<221> NAME/KEY: misc_feature
<222> LOCATION: (23)..(24)
<223> OTHER INFORMATION: DNA only

<400> SEQUENCE: 3
uucaguuauc acaguacuug uatt                                               24

<210> SEQ ID NO 4
<211> LENGTH: 21
<212> TYPE: RNA
<213> ORGANISM: Homo sapiens

<400> SEQUENCE: 4
uacaguacug ugauaacuga a                                                  21

<210> SEQ ID NO 5
<211> LENGTH: 25
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
<223> OTHER INFORMATION: DNA only

<400> SEQUENCE: 5
ccacacacuu ccuuacauuu ccatt                                              25

<210> SEQ ID NO 6
<211> LENGTH: 22
<212> TYPE: RNA
<213> ORGANISM: Homo sapiens

<400> SEQUENCE: 6
uggaauguaa ggaagugugu gg                                                 22

<210> SEQ ID NO 7
<211> LENGTH: 25

```
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
<223> OTHER INFORMATION: DNA only

<400> SEQUENCE: 7
auacauacuu cuuuacauuu ccatt                                        25

<210> SEQ ID NO 8
<211> LENGTH: 22
<212> TYPE: RNA
<213> ORGANISM: Homo sapiens

<400> SEQUENCE: 8
uggaauguaa agaagauguu au                                           22

<210> SEQ ID NO 9
<211> LENGTH: 25
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
<223> OTHER INFORMATION: DNA only

<400> SEQUENCE: 9
uaaccgauuu cagauggugu cuatt                                        25

<210> SEQ ID NO 10
<211> LENGTH: 22
<212> TYPE: RNA
<213> ORGANISM: Homo sapiens

<400> SEQUENCE: 10
uagcaccauc ugaaaucggu ua                                           22

<210> SEQ ID NO 11
<211> LENGTH: 26
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(24)
<223> OTHER INFORMATION: RNA only
<220> FEATURE:
<221> NAME/KEY: misc_feature
<222> LOCATION: (25)..(26)
<223> OTHER INFORMATION: DNA only

<400> SEQUENCE: 11
cacaaauucg gaucuacagg uguatt                                       26

<210> SEQ ID NO 12
```

```
<211> LENGTH: 23
<212> TYPE: RNA
<213> ORGANISM: Homo sapiens

<400> SEQUENCE: 12
uacccuguag auccgaauuu gug                                              23

<210> SEQ ID NO 13
<211> LENGTH: 26
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(24)
<223> OTHER INFORMATION: RNA only
<220> FEATURE:
<221> NAME/KEY: misc_feature
<222> LOCATION: (25)..(26)
<223> OTHER INFORMATION: DNA only

<400> SEQUENCE: 13
gaaacccagc agacaaugua ugcutt                                           26

<210> SEQ ID NO 14
<211> LENGTH: 23
<212> TYPE: RNA
<213> ORGANISM: Homo sapiens

<400> SEQUENCE: 14
agcuacauug ucugcugggu uuc                                              23

<210> SEQ ID NO 15
<211> LENGTH: 26
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(24)
<223> OTHER INFORMATION: RNA only
<220> FEATURE:
<221> NAME/KEY: misc_feature
<222> LOCATION: (25)..(26)
<223> OTHER INFORMATION: DNA only

<400> SEQUENCE: 15
accccuauca cgauuagcau uuaatt                                           26

<210> SEQ ID NO 16
<211> LENGTH: 23
<212> TYPE: RNA
<213> ORGANISM: Homo sapiens

<400> SEQUENCE: 16
uuaaugcuaa ucgugauagg ggu                                              23

<210> SEQ ID NO 17
<211> LENGTH: 26
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(24)
<223> OTHER INFORMATION: RNA only
```

```
<220> FEATURE:
<221> NAME/KEY: misc_feature
<222> LOCATION: (25)..(26)
<223> OTHER INFORMATION: DNA only

<400> SEQUENCE: 17
cuaccugcac uauaagcacu uuuatt                                          26

<210> SEQ ID NO 18
<211> LENGTH: 23
<212> TYPE: RNA
<213> ORGANISM: Homo sapiens

<400> SEQUENCE: 18
uaaagugcuu auagugcagg uag                                             23

<210> SEQ ID NO 19
<211> LENGTH: 25
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
<223> OTHER INFORMATION: DNA only

<400> SEQUENCE: 19
ucaacaucag ucugauaagu cuatt                                           25

<210> SEQ ID NO 20
<211> LENGTH: 22
<212> TYPE: RNA
<213> ORGANISM: Homo sapiens

<400> SEQUENCE: 20
uagcuuauca gacugauguu ga                                              22

<210> SEQ ID NO 21
<211> LENGTH: 24
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(22)
<223> OTHER INFORMATION: RNA only
<220> FEATURE:
<221> NAME/KEY: misc_feature
<222> LOCATION: (23)..(24)
<223> OTHER INFORMATION: DNA only

<400> SEQUENCE: 21
gcggaacuua gccacuguug aatt                                            24

<210> SEQ ID NO 22
<211> LENGTH: 21
<212> TYPE: RNA
<213> ORGANISM: Homo sapiens

<400> SEQUENCE: 22
uucacagugg cuaaguuccg c                                               21
```

```
<210> SEQ ID NO 23
<211> LENGTH: 25
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
<223> OTHER INFORMATION: DNA only

<400> SEQUENCE: 23
augcccuuuu aacauugcau cugtt                                           25

<210> SEQ ID NO 24
<211> LENGTH: 22
<212> TYPE: RNA
<213> ORGANISM: Homo sapiens

<400> SEQUENCE: 24
cagugcaaug uuaaaagggc au                                              22

<210> SEQ ID NO 25
<211> LENGTH: 68
<212> TYPE: RNA
<213> ORGANISM: Homo sapiens

<400> SEQUENCE: 25
ucgaagagcc aaauucuguc uccuuggaau guaaggaagu guguggacac caauggcuuu     60
cuagagcu                                                              68

<210> SEQ ID NO 26
<211> LENGTH: 25
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
<223> OTHER INFORMATION: DNA only

<400> SEQUENCE: 26
ccacacacuu ccuuacauuu ccatt                                           25

<210> SEQ ID NO 27
<211> LENGTH: 23
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(21)
<223> OTHER INFORMATION: RNA only
<220> FEATURE:
<221> NAME/KEY: misc_feature
<222> LOCATION: (22)..(23)
<223> OTHER INFORMATION: DNA only

<400> SEQUENCE: 27
```
acacacuucc uuacauuucc att                                            23

<210> SEQ ID NO 28
<211> LENGTH: 24
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(22)
<223> OTHER INFORMATION: RNA only
<220> FEATURE:
<221> NAME/KEY: misc_feature
<222> LOCATION: (23)..(24)
<223> OTHER INFORMATION: DNA only

<400> SEQUENCE: 28
ccacacacaa ccuuacauuc catt                                           24

<210> SEQ ID NO 29
<211> LENGTH: 69
<212> TYPE: RNA
<213> ORGANISM: Homo sapiens

<400> SEQUENCE: 29
ucgaagagcc aaauucuguc uccuuggaaa uguaaggaag uguguggaca ccaauggcuu    60
ucuagagcu                                                            69

<210> SEQ ID NO 30
<211> LENGTH: 59
<212> TYPE: RNA
<213> ORGANISM: Homo sapiens

<400> SEQUENCE: 30
ucgaagaaau auauuguuaa uacaguacug ugauaacuga acuaaucuu acacuggcu      59

<210> SEQ ID NO 31
<211> LENGTH: 24
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(22)
<223> OTHER INFORMATION: RNA only
<220> FEATURE:
<221> NAME/KEY: misc_feature
<222> LOCATION: (23)..(24)
<223> OTHER INFORMATION: DNA only

<400> SEQUENCE: 31
uucaguuauc acaguacuug uatt                                           24

<210> SEQ ID NO 32
<211> LENGTH: 22
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(20)
<223> OTHER INFORMATION: RNA only
<220> FEATURE:
<221> NAME/KEY: misc_feature
<222> LOCATION: (21)..(22)

```
<223> OTHER INFORMATION: DNA only

<400> SEQUENCE: 32
caguuaucad aguacuugua tt                                    22

<210> SEQ ID NO 33
<211> LENGTH: 21
<212> TYPE: RNA
<213> ORGANISM: Artificial Sequence
<220> FEATURE:
<223> OTHER INFORMATION: BASED ON HOMO SAPIENS

<400> SEQUENCE: 33
uucaguuauc acaguacugu a                                     21

<210> SEQ ID NO 34
<211> LENGTH: 59
<212> TYPE: RNA
<213> ORGANISM: Homo sapiens

<400> SEQUENCE: 34
ucgagaaaua uauuguuaau acaaguacug ugauaacuga acuaauucuu acacuggcu    59

<210> SEQ ID NO 35
<211> LENGTH: 66
<212> TYPE: DNA
<213> ORGANISM: Homo sapiens

<400> SEQUENCE: 35
tcgagagcca aattctgtct cctccacaca cttccttaca ttccaacacc aatggctttc   60
tagagc                                                              66

<210> SEQ ID NO 36
<211> LENGTH: 22
<212> TYPE: RNA
<213> ORGANISM: Homo sapiens

<400> SEQUENCE: 36
uggaauguaa ggaagugugu gg                                    22

<210> SEQ ID NO 37
<211> LENGTH: 56
<212> TYPE: DNA
<213> ORGANISM: Homo sapiens

<400> SEQUENCE: 37
tcgagaaata tattgttaat cagttatcac agtactgtac taattcttac actggc      56

<210> SEQ ID NO 38
<211> LENGTH: 21
<212> TYPE: RNA
<213> ORGANISM: Homo sapiens

<400> SEQUENCE: 38
uacaguacug ugauaacuga a                                     21

<210> SEQ ID NO 39
<211> LENGTH: 22
<212> TYPE: RNA
<213> ORGANISM: Homo sapiens

<400> SEQUENCE: 39
uggaauguaa ggaagugugu gg                                    22
```

```
<210> SEQ ID NO 40
<211> LENGTH: 25
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
<223> OTHER INFORMATION: DNA only

<400> SEQUENCE: 40
ccacaugcuu cuuuauaucc ccatt                                           25

<210> SEQ ID NO 41
<211> LENGTH: 24
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(22)
<223> OTHER INFORMATION: RNA only
<220> FEATURE:
<221> NAME/KEY: misc_feature
<222> LOCATION: (23)..(24)
<223> OTHER INFORMATION: DNA only

<400> SEQUENCE: 41
uggaauguaa ggaagugugu ggtt                                            24

<210> SEQ ID NO 42
<211> LENGTH: 26
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(24)
<223> OTHER INFORMATION: RNA only
<220> FEATURE:
<221> NAME/KEY: misc_feature
<222> LOCATION: (25)..(26)
<223> OTHER INFORMATION: DNA only

<400> SEQUENCE: 42
ccacacacuu ccuuacauua uccatt                                          26

<210> SEQ ID NO 43
<211> LENGTH: 24
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(22)
<223> OTHER INFORMATION: RNA only
<220> FEATURE:
<221> NAME/KEY: misc_feature
<222> LOCATION: (23)..(24)
<223> OTHER INFORMATION: DNA only

<400> SEQUENCE: 43
```
uggaauguaa ggaagugugu ggtt                                            24

<210> SEQ ID NO 44
<211> LENGTH: 26
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(24)
<223> OTHER INFORMATION: RNA only
<220> FEATURE:
<221> NAME/KEY: misc_feature
<222> LOCATION: (25)..(26)
<223> OTHER INFORMATION: DNA only

<400> SEQUENCE: 44
ccacacacuu cuuuauauua uccatt                                          26

<210> SEQ ID NO 45
<211> LENGTH: 25
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
<223> OTHER INFORMATION: DNA only

<400> SEQUENCE: 45
ccacacacuu ccuuacauuu ccatt                                           25

<210> SEQ ID NO 46
<211> LENGTH: 25
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
<223> OTHER INFORMATION: DNA only

<400> SEQUENCE: 46
ccacacacuu cuuuauauuu ccatt                                           25

<210> SEQ ID NO 47
<211> LENGTH: 24
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(22)
<223> OTHER INFORMATION: RNA only
<220> FEATURE:
<221> NAME/KEY: misc_feature
<222> LOCATION: (23)..(24)
<223> OTHER INFORMATION: DNA only

<400> SEQUENCE: 47

```
ccacacacuu ccuuacacac catt                                          24

<210> SEQ ID NO 48
<211> LENGTH: 24
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(22)
<223> OTHER INFORMATION: RNA only
<220> FEATURE:
<221> NAME/KEY: misc_feature
<222> LOCATION: (23)..(24)
<223> OTHER INFORMATION: DNA only

<400> SEQUENCE: 48
ccacacacuu cuuuauacac catt                                          24

<210> SEQ ID NO 49
<211> LENGTH: 24
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(22)
<223> OTHER INFORMATION: RNA only
<220> FEATURE:
<221> NAME/KEY: misc_feature
<222> LOCATION: (23)..(24)
<223> OTHER INFORMATION: DNA only

<400> SEQUENCE: 49
cucaguuauc acagugcuga ugtt                                          24

<210> SEQ ID NO 50
<211> LENGTH: 23
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(21)
<223> OTHER INFORMATION: RNA only
<220> FEATURE:
<221> NAME/KEY: misc_feature
<222> LOCATION: (22)..(23)
<223> OTHER INFORMATION: DNA only

<400> SEQUENCE: 50
uacaguacug ugauaacuga att                                           23

<210> SEQ ID NO 51
<211> LENGTH: 22
<212> TYPE: DNA
<213> ORGANISM: Artificial Sequence
<220> FEATURE:
<223> OTHER INFORMATION: BASED ON HOMO SAPIENS

<400> SEQUENCE: 51
uucgguuauc augguaccga ug                                            22

<210> SEQ ID NO 52
<211> LENGTH: 25
<212> TYPE: DNA
```

```
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
<223> OTHER INFORMATION: DNA only

<400> SEQUENCE: 52
uucaguuauc acaguacuuu guatt                                           25

<210> SEQ ID NO 53
<211> LENGTH: 25
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(23)
<223> OTHER INFORMATION: RNA only
<220> FEATURE:
<221> NAME/KEY: misc_feature
<222> LOCATION: (24)..(25)
<223> OTHER INFORMATION: DNA only

<400> SEQUENCE: 53
uucaguuauc augguacuuu guatt                                           25

<210> SEQ ID NO 54
<211> LENGTH: 24
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(22)
<223> OTHER INFORMATION: RNA only
<220> FEATURE:
<221> NAME/KEY: misc_feature
<222> LOCATION: (23)..(24)
<223> OTHER INFORMATION: DNA only

<400> SEQUENCE: 54
uucaguuauc acaguacuug uatt                                            24

<210> SEQ ID NO 55
<211> LENGTH: 24
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(22)
<223> OTHER INFORMATION: RNA only
<220> FEATURE:
<221> NAME/KEY: misc_feature
<222> LOCATION: (23)..(24)
<223> OTHER INFORMATION: DNA only

<400> SEQUENCE: 55
uucaguuauc augguacuug uatt                                            24

<210> SEQ ID NO 56
<211> LENGTH: 23
```

```
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(21)
<223> OTHER INFORMATION: RNA only
<220> FEATURE:
<221> NAME/KEY: misc_feature
<222> LOCATION: (22)..(23)
<223> OTHER INFORMATION: DNA only

<400> SEQUENCE: 56
uucaguuauc acaguaucgu att                                             23

<210> SEQ ID NO 57
<211> LENGTH: 23
<212> TYPE: DNA
<213> ORGANISM: Artificial Sequence
<220> FEATURE:
<223> OTHER INFORMATION: BASED ON HOMO SAPIENS
<220> FEATURE:
<221> NAME/KEY: misc_feature
<222> LOCATION: (1)..(21)
<223> OTHER INFORMATION: RNA only
<220> FEATURE:
<221> NAME/KEY: misc_feature
<222> LOCATION: (22)..(23)
<223> OTHER INFORMATION: DNA only

<400> SEQUENCE: 57
uucaguuauc augguaucgu att                                             23

<210> SEQ ID NO 58
<211> LENGTH: 21
<212> TYPE: RNA
<213> ORGANISM: Homo sapiens

<400> SEQUENCE: 58
uacaguacug ugauaacuga a                                               21
```